United States Patent
Hegedus et al.

(10) Patent No.: US 12,171,693 B2
(45) Date of Patent: Dec. 24, 2024

(54) METHOD OF CORRECTING HIGHER-ORDER ABERRATIONS USING LASER VISION CORRECTION

(71) Applicant: Alcon Inc., Fribourg (CH)

(72) Inventors: Imre Hegedus, Aliso Viejo, CA (US); Zsolt Bor, San Clemente, CA (US)

(73) Assignee: ALCON INC., Fribourg (CH)

(*) Notice: Subject to any disclaimer, the term of this patent is extended or adjusted under 35 U.S.C. 154(b) by 429 days.

(21) Appl. No.: 17/330,499

(22) Filed: May 26, 2021

(65) Prior Publication Data

US 2021/0369500 A1 Dec. 2, 2021

Related U.S. Application Data

(60) Provisional application No. 63/030,516, filed on May 27, 2020.

(51) Int. Cl.
*A61F 9/008* (2006.01)

(52) U.S. Cl.
CPC ........ *A61F 9/00829* (2013.01); *A61F 9/0084* (2013.01); *A61F 2009/00848* (2013.01); *A61F 2009/00851* (2013.01); *A61F 2009/00872* (2013.01); *A61F 2009/00897* (2013.01)

(58) Field of Classification Search
CPC ................ A61F 9/00829; A61F 9/0084; A61F 2009/00848; A61F 2009/00851; A61F 2009/00872; A61F 2009/00897; A61F 2009/0088
See application file for complete search history.

(56) References Cited

U.S. PATENT DOCUMENTS

| | | | |
|---|---|---|---|
| 6,271,914 B1 * | 8/2001 | Frey | A61B 3/107 356/124 |
| 7,972,325 B2 * | 7/2011 | Stark | A61B 3/1015 606/5 |
| 2003/0225399 A1 * | 12/2003 | Chernyak | A61F 9/00806 606/5 |
| 2009/0292275 A1 * | 11/2009 | Stevens | A61F 9/00806 606/5 |
| 2013/0211390 A1 * | 8/2013 | Bor | A61F 9/00829 606/5 |
| 2018/0008461 A1 * | 1/2018 | Fu | A61F 9/00829 |

FOREIGN PATENT DOCUMENTS

| | | |
|---|---|---|
| EP | 3427706 A1 | 1/2019 |
| WO | 2008014419 A2 | 1/2008 |
| WO | 2016049442 A1 | 3/2016 |

* cited by examiner

*Primary Examiner* — John R Downey

(57) ABSTRACT

The disclosure provides a method for correcting higher-order aberrations including providing a laser radiation. The method also includes controlling a location of a beam focal point of the laser radiation by a system of scanners and guiding the beam focal point in such a way that the location of the beam focal point is in a cornea of an eye. The method further includes introducing the laser radiation into the cornea of the eye. The method includes cutting a lenslet, wherein a thickness of the lenslet $t(X,Y)$ satisfies a following equation: $t(X,Y)=t_0+\Delta t(X,Y)/(n-1)$, where $\Delta t(X,Y)$ represents a higher-order wavefront elevation and $t_0$ represents the thickness of the lenslet having a spherical refractive power of D.

18 Claims, 8 Drawing Sheets

METHOD OF CORRECTING HIGHER-ORDER ABERRATIONS USING LASER VISION CORRECTION

TECHNICAL FIELD

The present invention generally relates to laser vision correction and, in particular, to a method of correcting higher-order aberrations using laser vision correction.

BACKGROUND

Refractive surgery such as laser eye surgery or laser vision correction has opened new possibilities for treating nearsightedness, farsightedness, astigmatism, and other conditions of the eye. Laser eye surgery techniques such as protorefractive keratectomy (PRK), laser-assisted in situ keratomileusis (LASIK), laser epithlelial keratomileusis (LASEK), automated lamellar keratoplasty (ALK), and small incision lenticule extraction (SMILE) have been developed to treat such conditions that are also known as lower-order aberrations (such as myopia, hyperopia, presbyopia, and astigmatism). Higher-order aberrations (HOAs) are more complex refractive errors involving abnormal curvature and distortion of a cornea and crystalline lens than the lower-order aberrations. As such, treating HOAs requires different approaches.

SUMMARY

The disclosure provides a method for correcting higher-order aberrations including providing a laser radiation. The method also includes controlling a location of a beam focal point of the laser radiation by a system of scanners and guiding the beam focal point in such a way that the location of the beam focal point is in a cornea of an eye. The method further includes introducing the laser radiation into the cornea of the eye. The method includes cutting a lenslet, wherein a thickness of the lenslet $t(X,Y)$ satisfies a following equation: $t(X,Y)=t_0+\Delta t(X,Y)/(n-1)$, where $\Delta t(X,Y)$ represents a higher-order wavefront elevation and $t_0$ represents the thickness of the lenslet having a spherical refractive power of D.

The above method for correcting higher-order aberrations may be further characterized by one or more of the following additional steps, which may be combined with one another or any other portion of the description in this specification, including specific examples, unless clearly mutually exclusive:

i) the laser radiation may be a femtosecond laser;
ii) the system of scanners may comprise at least one transverse control element and at least one longitudinal control element;
iii) the higher-order wavefront elevation may be measured with a wavefront meter or a corneal topographer;
iv) the thickness of the lesnlet $t_0$ may correct a spherical error of the eye.
v) the higher-order wavefront elevation $\Delta t(X,Y)$ may correct the higher-order aberrations;
vi) the higher-order wavefront elevation $\Delta t(X,Y)$ may be expressed using Zernike, Fourier, wavelet, Wiegner, or other orthogonal polynomials;
vii) the lenslet may be cut using a spiral scanning of the femtosecond laser beam; and
viii) the system of scanners may include 3D scanners.

The disclosure provides a method for correcting higher-order aberrations including providing a laser radiation. The method also includes controlling a location of a beam focal point of the laser radiation by a scanner and guiding the beam focal point in such a way that the location of the beam focal point is in a cornea of an eye. The method further includes introducing the laser radiation into the cornea of the eye. The method includes cutting a lenslet, wherein a radius of the lenslet at any X,Y point satisfies a following equation: $\Delta r(X,Y)=\Delta t(X,Y)*R/r$, where $\Delta t(X,Y)$ represents a higher-order wavefront elevation, R represents a curvature of the cornea, and r/R represents a slope of the curvature of the cornea.

The above method for correcting higher-order aberrations may be further characterized by one or more of the following additional steps, which may be combined with one another or any other portion of the description in this specification, including specific examples, unless clearly mutually exclusive:

i) the laser radiation may be a femtosecond laser.

The disclosure provides a pulse laser device for correcting higher-order aberrations including a laser source that provides a laser radiation. The pulse laser device also includes a scanner that controls a location of a beam focal point of the laser radiation and guides the beam focal point in such a way that the location of the beam focal point is in a cornea of an eye. The pulse laser device further includes a computer that generates instructions to the laser source and scanner to introduce the laser radiation into the cornea of the eye to cut a lenslet, wherein a thickness of the lenslet $t(X,Y)$ satisfies a following equation: $t(X,Y)=t_0+\Delta t(X,Y)/(n-1)$, where $\Delta t(X,Y)$ represents a higher-order wavefront elevation and $t_0$ represents the thickness of the lenslet having a spherical refractive power of D.

The above pulse laser device for correcting higher-order aberrations may be further characterized by one or more of the following additional elements, which may be combined with one another or any other portion of the description in this specification, including specific examples, unless clearly mutually exclusive;

i) the laser radiation may be a femtosecond laser;
ii) the scanner may comprise at least one transverse control element and at least one longitudinal control element;
iii) the higher-order wavefront elevation may be measured with a wavefront meter or a corneal topographer;
iv) the thickness of the lenslets $t_0$ may correct a spherical error of the cornea;
v) the higher-order wavefront elevation $\Delta t(X,Y)$ may correct the higher-order aberrations;
vi) the higher-order wavefront elevation $\Delta t(X,Y)$ may be a Zernike or Fourier polynomials;
vii) the lenslet may be cut using a spiral scanning of the femtosecond laser beam; and
viii) the scanner may be a 3D scanner.

BRIEF DESCRIPTION OF THE DRAWINGS

Embodiments of the present disclosure are described by way of example in greater detail with reference to the attached figures, which are not necessarily to scale, and in which.

DETAILED DESCRIPTION

Embodiments of the present disclosure are directed to laser vision correction. More particularly, embodiments of the present disclosure are directed to a method of cutting a lenslet (a portion of the cornea that is removed during vision correction surgery and also called a lenticule) using a femtosecond laser to correct higher-order aberrations (HOAs). Embodiments of the present disclosure allow for correcting HOAs without creating a flap by cutting through the corneal epithelium and Bowman's membrane with a femtosecond laser.

Figure 1:
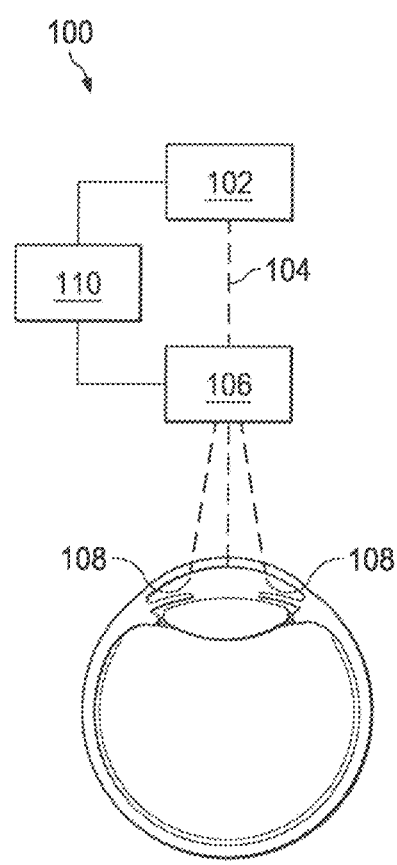
FIG. 1 is a schematic diagram of a pulsed laser system.

FIG. 1 is a schematic diagram of a pulsed laser system 100 for eye surgery, including refractive eye surgery such as laser vision correction. The pulsed laser system 100 may be a separate surgical tool, or part of a larger eye surgery system, which may include other laser systems, patient or eye positioning systems, viewing systems, or any combinations thereof. In particular, the pulsed laser system 100 may be part of a surgical suite designed to provide substantially all computer-assisted devices for performing a given eye surgery.

A pulsed laser system 100 includes a laser source 102, which generates laser radiation 104. The laser radiation 104 (a laser beam) may include laser radiations used to cut eye tissues including such as corneal stroma through vaporization (a laser scalpel). For example, the laser radiation 104 generated from the laser source 102 may include a femtosecond, picosecond, nanosecond, or attosecond laser.

A pulsed laser system 100 includes a scanner 106 for controlling a radiation focal points 108 during surgery in the cornea of the patient's eye. The scanner 106 provides transverse control axis (X- and Y-axes), longitudinal control axis (Z-axis) of radiation focal points 108. "Transverse" refers to a direction at a right angle to the propagation direction of laser beam 104. "Longitudinal" refers to the propagation direction of the laser beam 104. The scanner 106 may be 3D scanner.

Although the pulsed laser system 100 in FIG. 1 does not show various other radiation control components, the scanner 106 may control radiation focal points 108 in a longitudinal direction using a longitudinal control element. For example, longitudinal control element may include a longitudinally adjustable lens. Alternatively, longitudinal control element may include a variable refractive power lens. Also, alternatively, longitudinal control element may include a deformable mirror. Further, the scanner 106 may contain more than one transverse control element, more than one longitudinal control element, or more than one of both. In addition, the transverse control element and the longitudinal control element may be separate devices. Although scanner 106 shown in FIG. 1 is depicted as one component, such a configuration is merely provided for illustrative purposes. The embodiments of the present disclosure may be configured to include multiple scanners (a system of scanners) to allow for more precise control of the radiation focal points 108.

The laser source 102 and scanner 106 are controlled by computer 110. For example, the computer 110 may control which wavelength of laser radiation 104 is generated from the laser source 102. For instance, the computer may configure the laser source 102 to generate a femtosecond laser 104. Further, the computer 110 may control the length of the laser radiation 104. Additionally, the computer 110 may control the scanner 106 to change movements of the radiation focal points 108.

The computer 110 includes at least a processing resource able to execute code to generate instructions to control a lenslet cut geometry and a lenslet cut location in the cornea of a patient's eye. The computer 110 may be in physical or wireless communication with laser source 102 and scanner 106. The computer 110 may further include a memory, particularly a memory for storing instructions for the processing resource, a communications module for communicating with laser source 102 and scanner 106, and other components.

For simplicity, not all potential components of the pulsed laser system 100 are illustrated in FIG. 1. For example, the pulsed laser system may include various components for directing, focusing, or otherwise manipulating laser beam, such as scanners, mirrors, beam expanders, or lenses. The pulsed laser system 100 may further include housings and other equipment to protect and position its components as well as patient-interface peripherals, which may be disposable.

Figure 2A:
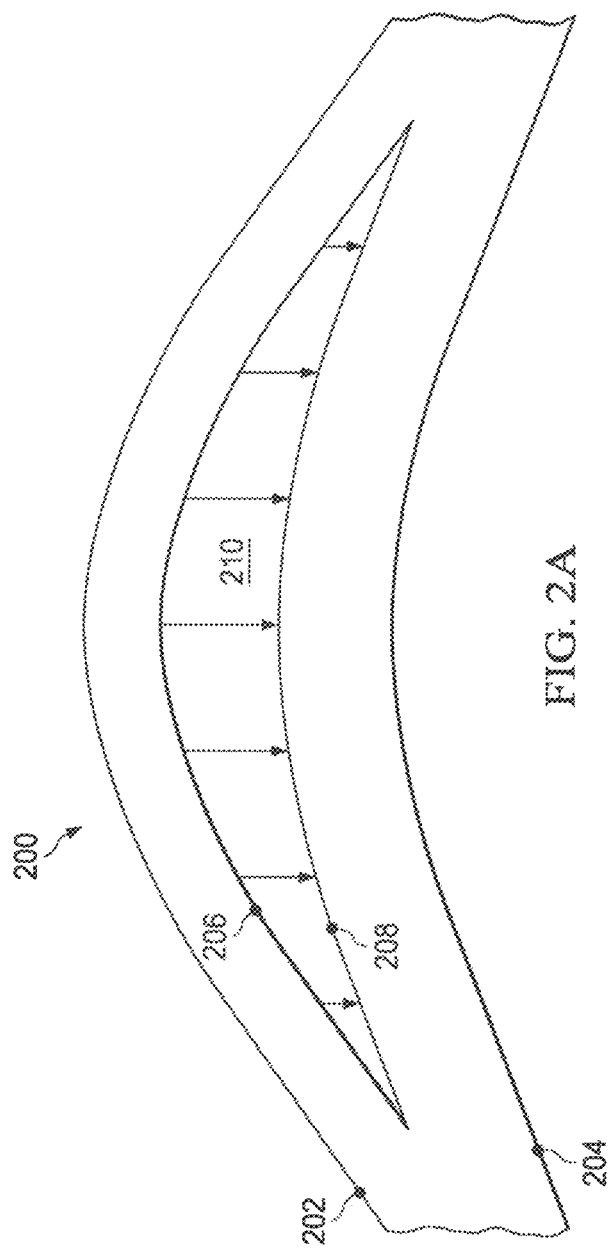
FIG. 2A is an illustration of a cross-sectional view of a cornea depicting a lenslet cut geometry for a small incision lenslet extraction procedure.

Referring now to FIG. 2A, a schematic depiction 200 of cut geometry for a small incision lenslet extraction procedure (such as SMILE®) is described. The human eye has a cornea, which is a transparent front part of the eye that covers the iris, pupil, and anterior chamber. For laser vision correction surgery, a portion of stroma (such as lenslet 210) within the cornea is removed to change a thickness of the patient's cornea to correct vision. The schematic depiction of cut geometry shown in FIG. 2A is a cross-sectional view of a cornea of a human eye. In general, for a SMILE® procedure, a lenslet 210 is created with a femtosecond laser in a shape corresponding to a desired refractive correction. The femtosecond incisions for the SMILE® procedure include four cuts: 1) cornea posterior cut; 2) side cut for the lenslet; 3) cap cut; and 4) side cut for the opening incision. The four cuts are performed in succession in an integrated manner. Then, the lenslet is subsequently accessed and removed through the opening incision. The cornea includes anterior cornea 202 and posterior cornea 204. The lenslet cut creates anterior spherical surface 206 of the lenslet 210 and posterior spherical surface 208 of the lenslet 210.

Figure 2B:
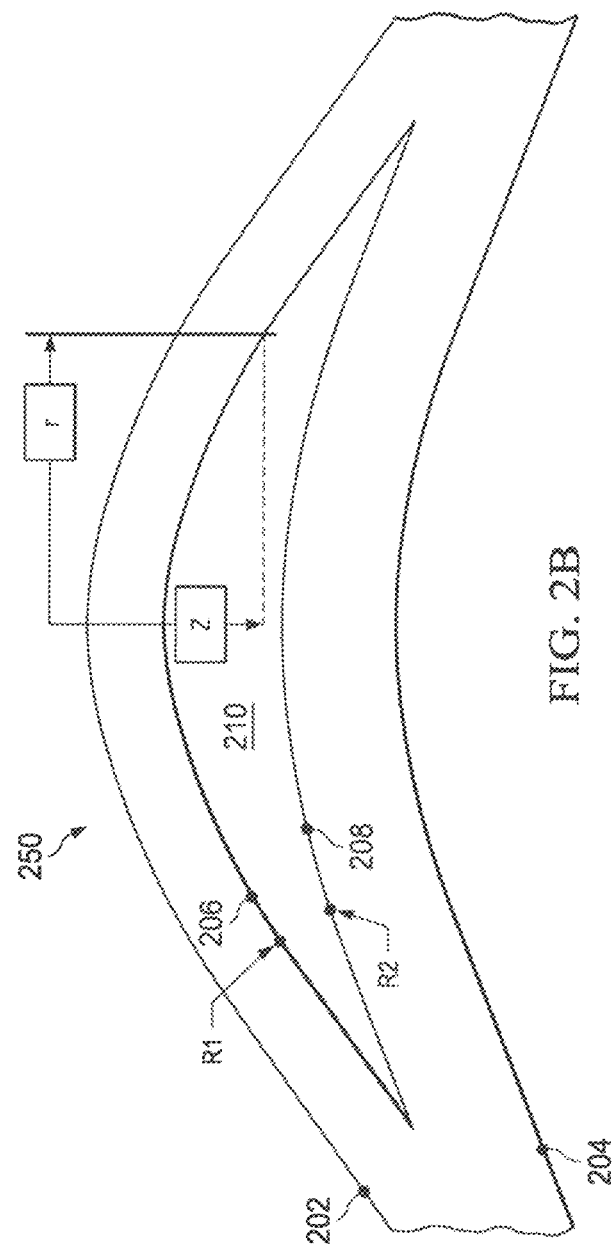
FIG. 2B is an illustration of a cross-sectional view of a cornea depicting a lenslet cut geometry for a small incision lenslet extraction procedure with respect to axes.

Referring now to FIG. 2B, a schematic depiction 250 of cut geometry for small incision lenslet extraction procedure (such as SMILE®) with respect to X-, Y-, and Z-axes is described. The lenslet is cut using a femtosecond laser. The spatial position of the laser radiation is controlled by three scanners: X-, Y-, and Z-scanners.

In general, X and Y scanners are galvanometric scanners. The lenslet is cut using spiral scanning of the femtosecond laser beam. The spiral is typically nearly a circle, because the radial line separation of consecutive spirals is around 5 um and the radius of the scanning is several thousand microns. For example, a diameter of a circle may be 4 mm (such as 4000 μm). Thus, the next outer circle of the spiral would have a diameter of 4010 μm.

The spherical refractive power of the lenslet is determined by the radii of the curvature of the anterior R1 and posterior R2 curvature of the lenslet surface as defined by the following equation:

$$D=(n-1)*(1/R2-1/R1) \quad \text{(eq 1)}$$

where D is the spherical refractive power of the lenslet and n is the refractive index of the cornea.

A thickness of the lenslet $t_0$ at the radial position r can be calculated by the following equation:

$$t_0=0.5*r^2(1/R2-1/R1)=(r^2/2)*D/(n-1) \quad \text{(eq 2)}$$

The Z scanner is typically an axially adjustable telescope. Due to mechanical inertia the Z scanner is slow and not able change position, speed, or acceleration nearly as rapidly as the scanners movable in the x and y planes. However, the circle time of scanning in Z axis is about 20 ms and within 20 ms, the Z position can be moved by a few microns, allowing the lenslet to be cut with a spherical shape.

Surfaces derived from a high order azimuthal Zernike polynomial presently cannot be cut using the Z scanner of femtosecond laser, since the rotation time of a Φ=5 mm circle having a typical 5 μm spot separation at 150 kHz laser rep rate=T=5000*π/(5*150000)=21 ms. Within 21 ms the Z scanner is incapable of moving up and down several times to cut a high order azimuthal surface.

Figure 3:
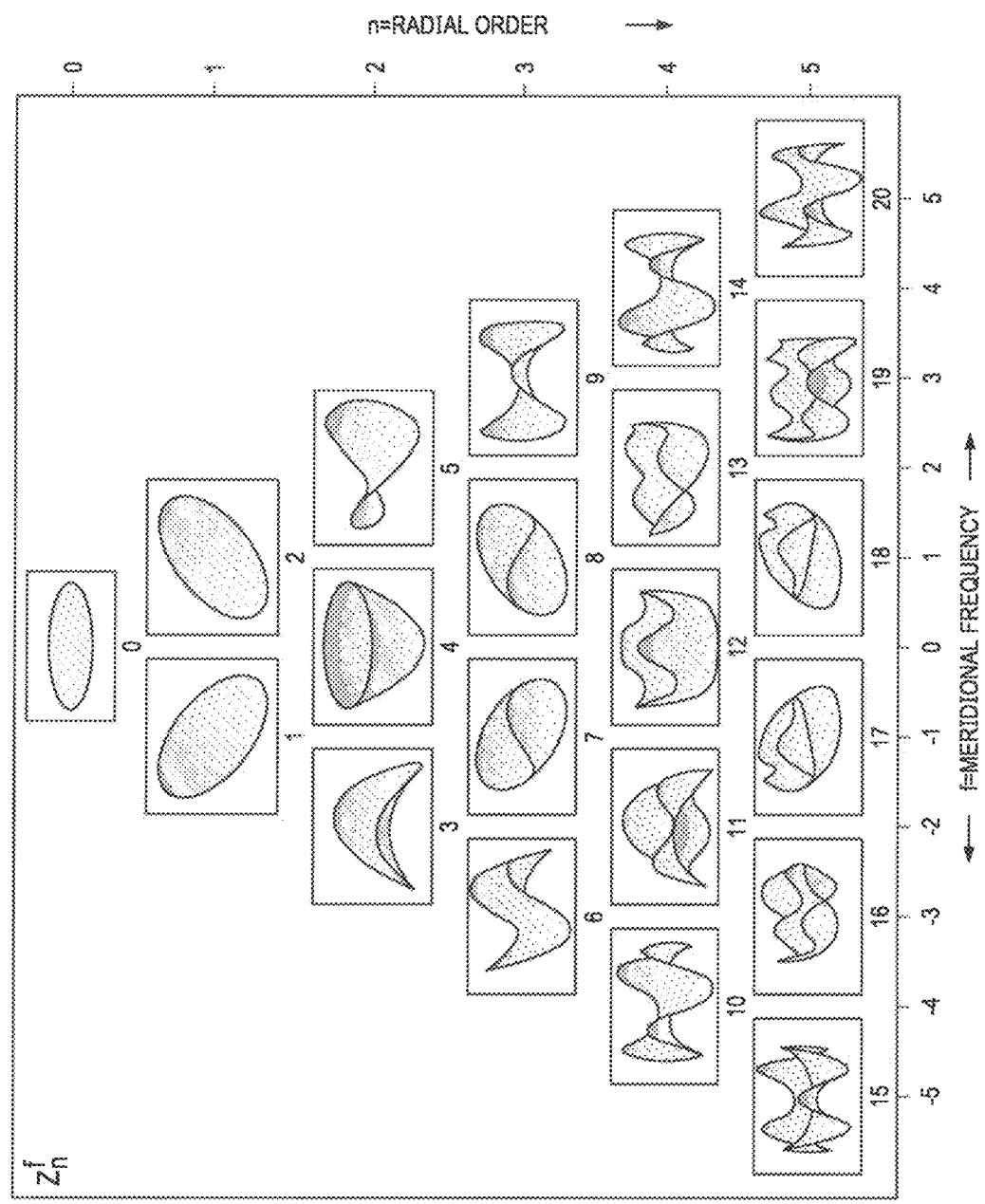
FIG. 3 illustrates aberration modes based on Zernike polynomial functions.

Now referring to FIG. 3, aberration modes based on Zernike polynomial functions are illustrated. Aberrations are focusing errors that prohibit the formation of high resolution. One of the ways to characterize the aberrations includes wavefront aberrations, which characterizes complex optical errors in focus produced by an optical system. The Zernike polynomial series is used to decompose complex wavefront aberrations into a collection of polynomial basis functions (such as modes), which are shown in FIG. 3.

Each Zernike mode includes two components: 1) radial order (n) and 2) meridional frequency (f). In ophthalmology, radial orders of Zernike polynomial series are categorized as either low-order aberrations or high-order abrasions. Low-order aberrations are Zernike modes having second order or lower (n≤2). High-order aberrations are Zernike modes having third order or higher (n≥3). Low-order aberrations which correspond to Zernike defocus (4 in FIG. 3) and astigmatism modes (3 and 5 in FIG. 3) are typically corrected with prescription spectacle lenses or contact lenses, while correction of high-order aberrations requires more complex procedures. The higher the radial order and/or meridional frequency is, the more complex a Zernike polynomial mode becomes. Cutting a lenslet for one of the high-order aberrations which is shown in FIG. 3 is an arduous task with a slow z scanner of the femtosecond laser.

Figure 4A:
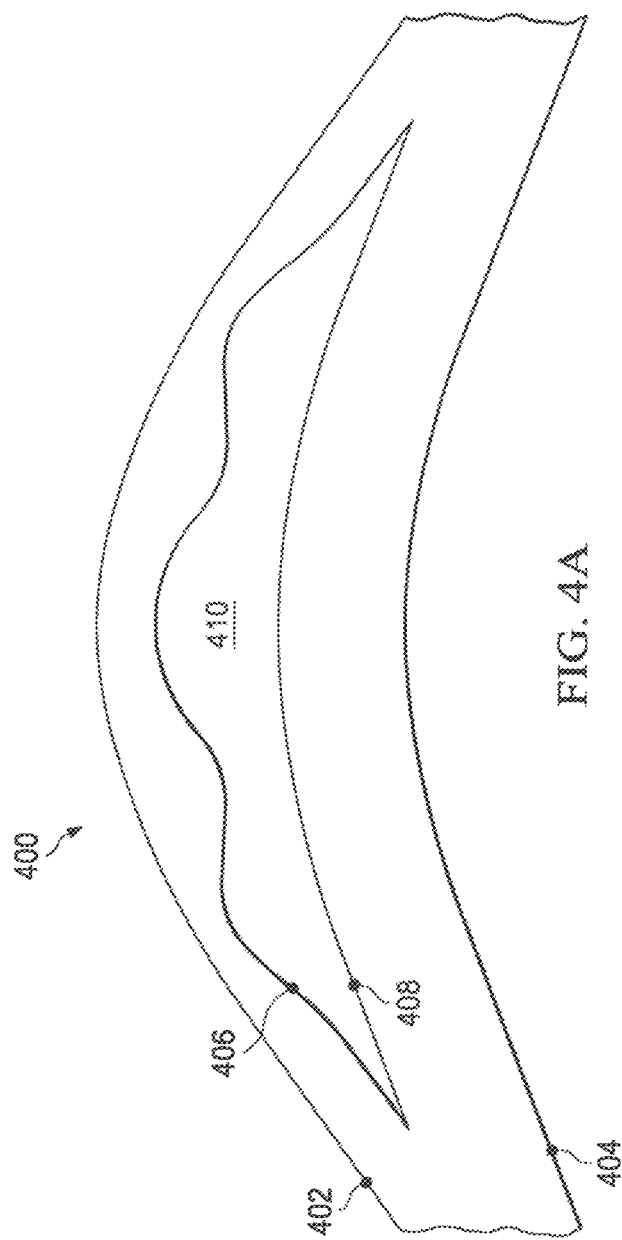
FIG. 4A is an illustration of a cross-sectional view of a cornea depicting a lenslet cut geometry for higher-order aberrations.

Now referring to FIG. 4A, an illustration depicting a lenslet cut geometry, in accordance with one or more embodiments of the present disclosure is shown. The schematic depiction of cut geometry shown in FIG. 4A is a cross-sectional view of a cornea. In one embodiment, the lenslet 410 which corrects for high-order aberrations may be cut. For example, the lenslet 410 may include multiple high-order Zernike polynomial modes. In this regard, the lenslet 410 does not simply have a spherical shape such as shown in FIGS. 2A and 2B. The cornea includes anterior cornea 402 and posterior cornea 404. The lenslet cut 410 creates anterior spherical surface 406 of the lenslet 410 and posterior spherical surface 408 of the lenslet 410.

In some embodiments, a thickness of the lenslet 410 which corrects higher-order aberrations can be calculated and a surface of the lenslet having a radius of curvature R is cut as follows:

The typical radial separation of two consecutive spiral cut RS is about 5 μm. To have a radius of curvature of the lenslet surface R, the vertical step (VS) should be $$VS=r/R*RS \quad \text{(eq 3)}$$

where r/R is the slope of the R surface at the position of r. To correct the HOA, the thickness of the lenslet should be changed to $$t(X,Y)=t_0+\Delta t(X,Y)/(n-1) \quad \text{(eq 4)}$$

where Δt(X,Y) is the HOA wavefront elevation measured with the wavefront meter or corneal topographer. It is noted that to is the thickness of the lenslet having a spherical refractive power of D which is responsible for correcting the spherical error. It is further noted that Δt(X,Y) is responsible for correcting the HOAs. Δt(X,Y) is typically described either with Zernike or Fourier polynomials.

Figure 4B:
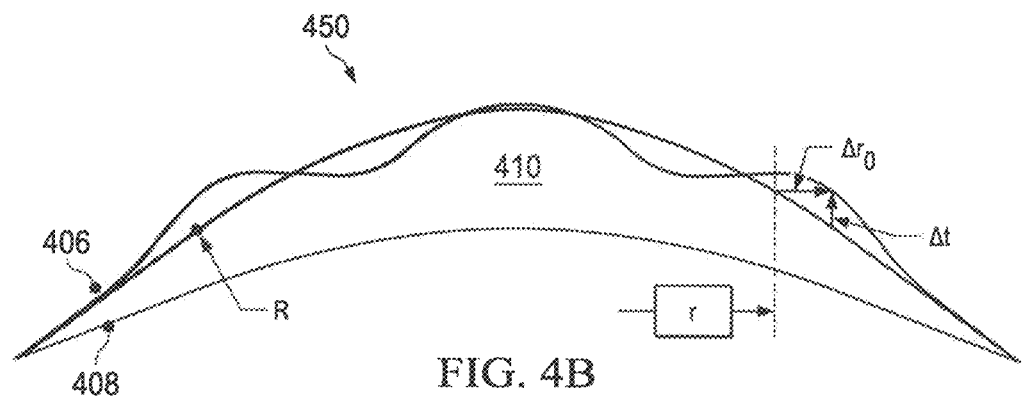
FIG. 4B is an illustration of a cross-sectional view of cornea depicting a lenslet cut geometry for higher-order aberrations with respect to axes.

FIG. 4B is an illustration depicting a lenslet cut geometry for higher-order aberrations with respect to axes, in accordance with one or more embodiments of this disclosure. As described in FIG. 4B, it is noted that by increasing the radius of the scanning by Δr the thickness of the lenslet is increasing by $$\Delta t=\Delta r*[\text{slope of the } R \text{ surface}] \quad \text{(eq 5)}$$

where the slope of the R curve is r/R, for example. Then, Δt may be expressed as $$\Delta t=\Delta r*r/R \quad \text{(eq6)}$$

Thus, in order to correct the HOA, the radius on the scanning at any X,Y point should be increased by $$\Delta r(X,Y)=\Delta t(X,Y)*R/r \quad \text{(eq 7)}$$

Figure 5:
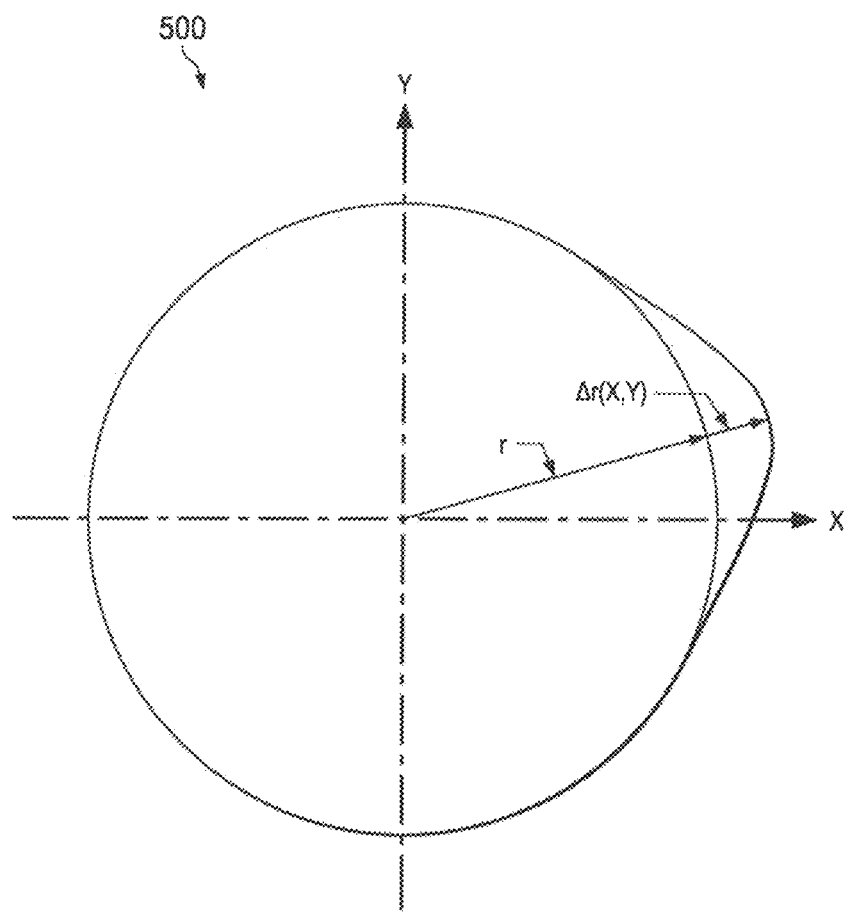
FIG. 5 is a schematic plan view of a cornea illustrating a lenslet cutting geometry for higher-order aberrations.

FIG. 5 is a schematic plan view 500 of a cornea illustrating a lenslet cutting geometry, in accordance with one or more embodiments of the present disclosure. In one embodiment, in order to correct the HOA, the radius on the scanning at any X,Y point may be increased by Δr(X,Y)=Δt(X,Y)*R/r, as described hereinbefore. Since radial scanning with X- and Y-axes scanners is fast, cutting the lenslet geometry including high-order aberrations may not need a change in Z-coordination. Therefore, embodiments of the present disclosure may allow for correcting the HOA without rapidly changing Z-coordinate when scanning.

Figure 6:
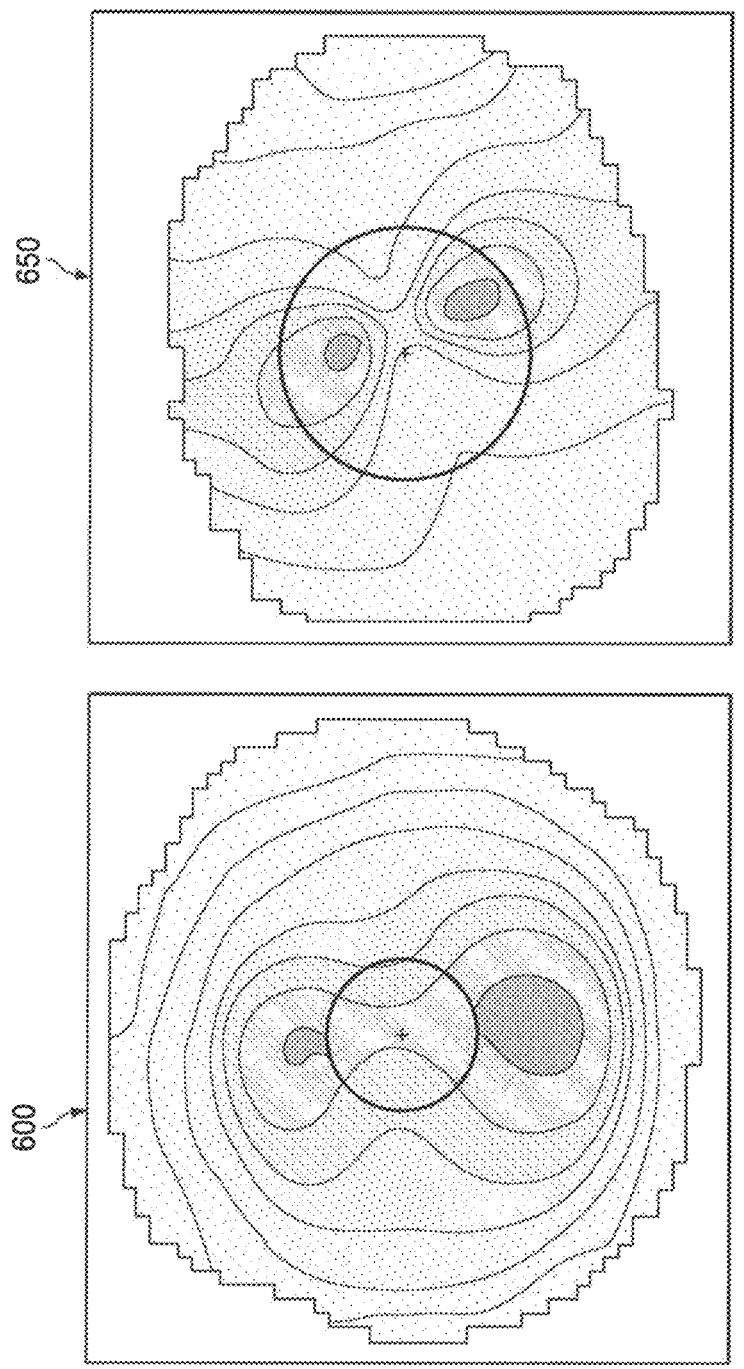
FIG. 6 illustrates wavefront elevation maps generated from a wavefront meter and corneal topographer.

FIG. 6 is illustrations of wavefront elevation maps (600 and 650) generated from wavefront meter or a corneal topographer. In one embodiment, a calculation of radius on the scanning at any X,Y point Δr(X,Y) to correct the HOA may require a wavefront elevation map using a wavefront meter or a corneal topographer. Wavefront elevation maps reveal any irregularity of corneal surface.

Figure 7:
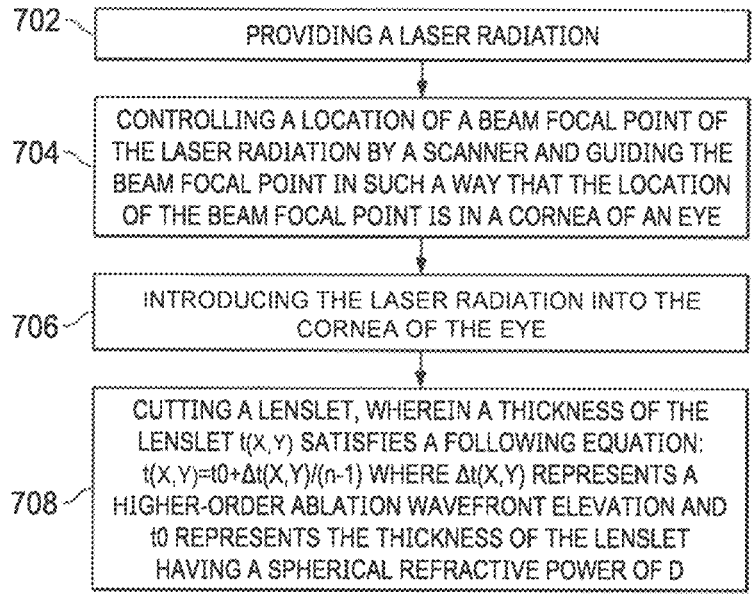
FIG. 7 illustrates a method for correcting higher-order aberrations.

FIG. 7 illustrates a method for correcting higher-order aberrations, in accordance with one or more embodiments of the present disclosure. The pulse laser device for correcting higher-order aberrations used in this method may be described in FIGS. 4A-5. It is noted that all of the steps shown in FIG. 7 are not essential to practice the method. One or more steps may be omitted from or added to the method illustrated in FIG. 7, and the method can still be practiced within the scope of this embodiment.

The method shown in FIG. 7 generally includes providing a laser radiation. The method further includes controlling a location of a beam focal point of the laser radiation by a scanner and guiding the beam focal point in such a way that the location of the beam focal point is in a cornea of an eye. The method further includes introducing the laser radiation into the cornea of the eye. The method further includes cutting a lenslet, wherein a thickness of the lenslet t(X,Y) satisfies a following equation:

$$t(X,Y)=t_0+\Delta t(X,Y)/(n-1) \quad \text{(eq 4)}$$

where $\Delta t(X,Y)$ represents a higher-order wavefront elevation and $t_0$ (eq 2) represents the thickness of the lenslet having a spherical refractive power of D.

Figure 8:
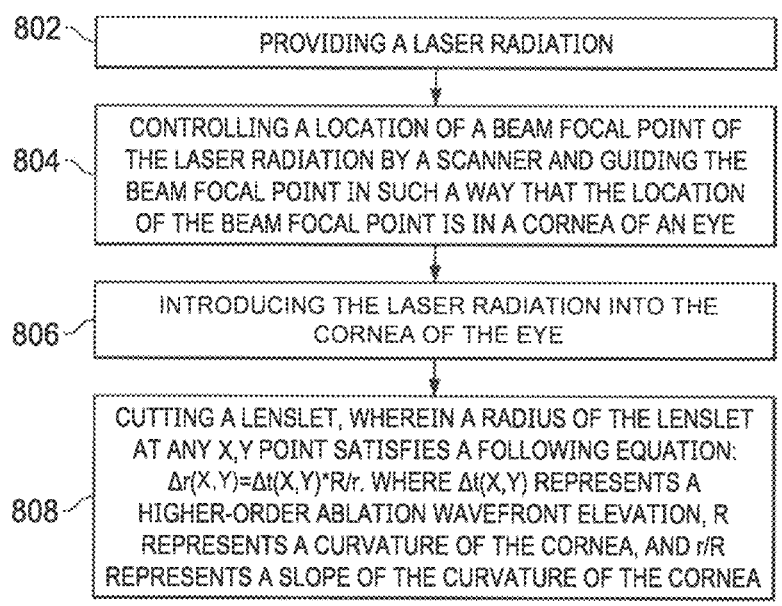
FIG. 8 illustrates another variation of the method for correcting higher-order aberrations.

FIG. 8 illustrates another variation of the method for correcting higher-order aberrations, in accordance with one or more embodiments of the present disclosure. The pulse laser device for correcting higher-order aberrations used in this method may be described in FIGS. 4A-5. It is noted that all of the steps shown in FIG. 8 are not essential to practice the method. One or more steps may be omitted from or added to the method illustrated in FIG. 8, and the method can still be practiced within the scope of this embodiment.

The method shown in FIG. 8 generally includes providing a laser radiation. The method further includes controlling a location of a beam focal point of the laser radiation by a scanner and guiding the beam focal point in such a way that the location of the beam focal point is in a cornea of an eye. The method further includes introducing the laser radiation into the cornea of the eye. The method further includes cutting a lenslet, wherein a radius of the lenslet at any X,Y point satisfies a following equation:

$$\Delta r(X,Y)=\Delta t(X,Y)*R/r \quad \text{(eq 7)}$$

where $\Delta t(X,Y)$ represents a higher-order wavefront elevation, R represents a curvature of the cornea, and r/R represents a slope of the curvature of the cornea.

Although this disclosure has been described in terms of certain embodiments, modifications (such as substitutions, additions, alterations, or omissions) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

What is claimed:

1. A method for correcting higher-order aberrations, comprising:
   providing a laser radiation;
   controlling a location of a beam focal point of the laser radiation by a system of scanners and guiding the beam focal point in such a way that the location of the beam focal point is in a cornea of an eye;
   introducing the laser radiation into the cornea of the eye; and
   cutting a lenslet:
      a thickness of the lenslet t(X,Y) satisfying a following equation:

$$t(X,Y)=t_0+\Delta t(X,Y)/(n-1)$$

where $\Delta t(X,Y)$ represents a higher-order wavefront elevation for correcting a higher order aberration, $t_0$ represents the thickness of the lenslet having a spherical refractive power of D for correcting a spherical error, and n represents a refractive index of the cornea; and
   the lenslet having an anterior lenslet surface, a cross-section of the lenslet showing the anterior lenslet surface having a plurality of convex curves and having a plurality of concave curves, each convex curve of the plurality of convex curves being convex relative to an anterior corneal surface, each concave curve of the plurality of concave curves being concave relative to the anterior corneal surface.

2. The method of claim 1, wherein the laser radiation is provided by a femtosecond laser.

3. The method of claim 1, wherein the system of scanners comprises at least one transverse control element and at least one longitudinal control element.

4. The method of claim 1, wherein the higher-order wavefront elevation is measured with a wavefront meter or a corneal topographer.

5. The method of claim 1, wherein the thickness of the lenslet $t_0$ corrects a spherical error of the eye.

6. The method of claim 1, wherein the higher-order wavefront elevation $\Delta t(X,Y)$ is expressed using Zernike, Fourier, wavelet, Wiegner, or other orthogonal polynomials.

7. The method of claim 1, wherein the lenslet is cut using a spiral scanning of the laser radiation.

8. The method of claim 1, wherein the system of scanners includes a 3D scanner.

9. The method of claim 1:
   the plurality of convex curves comprising a first peripheral convex curve, a central convex curve, and a second peripheral convex curve;
   the plurality of concave curves comprising a first concave curve and a second concave curve; and
   the first peripheral convex curve coupled to the first concave curve, the first concave curve coupled to the central convex curve, the central convex curve coupled to the second concave curve, and the second concave curve coupled to the second peripheral convex curve.

10. A pulse laser device for correcting higher-order aberrations, comprising:
   a laser source that provides a laser radiation;
   a scanner that controls a location of a beam focal point of the laser radiation and guides the beam focal point in such a way that the location of the beam focal point is in a cornea of an eye; and
   a computer that generates instructions to the laser source and scanner to introduce the laser radiation into the cornea of the eye to cut a lenslet:
      a thickness of the lenslet t(X,Y) satisfying a following equation:

$$t(X,Y)=t_0+\Delta t(X,Y)/(n-1)$$

where $\Delta t(X,Y)$ represents a higher-order wavefront elevation for correcting a higher order aberration, $t_0$ represents the thickness of the lenslet having a spherical refractive power of D for correcting a spherical error, and n represents a refractive index of the cornea; and
   the lenslet having an anterior lenslet surface, a cross-section of the lenslet showing the anterior lenslet surface having a plurality of convex curves and having a plurality of concave curves, each convex curve of the plurality of convex curves being convex relative to an anterior corneal surface, each concave curve of the plurality of concave curves being concave relative to the anterior corneal surface.

11. The pulse laser device of claim 10, wherein the laser source is a femtosecond laser.

12. The pulse laser device of claim 10, wherein the scanner comprises at least one transverse control element and at least one longitudinal control element.

13. The pulse laser device of claim 10, wherein the higher-order wavefront elevation is measured with a wavefront meter or a corneal topographer.

14. The pulse laser device of claim 10, wherein the thickness of the lenslet $t_0$ corrects a spherical error of the cornea.

15. The pulse laser device of claim 10, wherein the higher-order wavefront elevation $\Delta t(X,Y)$ is a Zernike or Fourier polynomials.

16. The pulse laser device of claim 10, wherein the lenslet is cut using a spiral scanning of the laser radiation.

17. The pulse laser device of claim 10, wherein the scanner is a 3D scanner.

18. The pulse laser device of claim 10:
the plurality of convex curves comprising a first peripheral convex curve, a central convex curve, and a second peripheral convex curve;
the plurality of concave curves comprising a first concave curve and a second concave curve; and
the first peripheral convex curve coupled to the first concave curve, the first concave curve coupled to the central convex curve, the central convex curve coupled to the second concave curve, and the second concave curve coupled to the second peripheral convex curve.

* * * * *